United States Patent
Hung et al.

(10) Patent No.: US 10,174,322 B2
(45) Date of Patent: Jan. 8, 2019

(54) SHORT INTERFERING RNA FOR TREATING CANCER

(71) Applicants: DCB-USA LLC, New Castle County, Wilmington, DE (US); NATIONAL CHENG KUNG UNIVERSITY, Tainan (TW)

(72) Inventors: Liang-Yi Hung, Tainan (TW); Chien-Hsien Lai, Tainan (TW); Ta-Chien Tseng, Tainan (TW); Jeng-Chang Lee, Tainan (TW); Bo-Wen Lin, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 15/549,174

(22) PCT Filed: Feb. 23, 2016

(86) PCT No.: PCT/US2016/019048
§ 371 (c)(1),
(2) Date: Aug. 7, 2017

(87) PCT Pub. No.: WO2016/137937
PCT Pub. Date: Sep. 1, 2016

(65) Prior Publication Data
US 2018/0037888 A1 Feb. 8, 2018

Related U.S. Application Data

(60) Provisional application No. 62/120,355, filed on Feb. 24, 2015.

(51) Int. Cl.
*A61K 31/70* (2006.01)
*C07H 21/02* (2006.01)
*C07H 21/04* (2006.01)
*C12N 15/113* (2010.01)
*A61K 9/127* (2006.01)
*A61K 48/00* (2006.01)

(52) U.S. Cl.
CPC ............ *C12N 15/113* (2013.01); *A61K 9/127* (2013.01); *C07H 21/04* (2013.01); *A61K 48/00* (2013.01); *C12N 2310/14* (2013.01); *C12N 2310/3231* (2013.01)

(58) Field of Classification Search
None
See application file for complete search history.

(56) References Cited

U.S. PATENT DOCUMENTS

2007/0031844 A1* 2/2007 Khvorova ............ A61K 31/713
435/6.11

* cited by examiner

*Primary Examiner* — Sean McGarry

(57) ABSTRACT

Disclosed herein is novel double-stranded short interfering ribonucleic acid (siRNA) capable of suppressing the translation of Aurora-A mRNA. Also disclosed are use of the novel siRNA as disclosed herein for manufacturing a medicament suitable for treating a cancer, which is mediated through epidermal growth factor receptor (EGFR) signaling. Accordingly, a pharmaceutical composition comprising the disclosed novel siRNA molecules is provided; as well as a method of treating a subject suffering from EGFR-mediated cancer via administering to the subject the disclosed novel siRNA molecule.

6 Claims, 7 Drawing Sheets
Specification includes a Sequence Listing.

(A)

(B)

1. siLNA 5 nM
2. siLNA-2 5 nM

SHORT INTERFERING RNA FOR TREATING CANCER

CROSS-REFERENCE TO RELATED APPLICATIONS

This application relates to and claims the benefit of U.S. Provisional Application No. 62/120,355, filed Feb. 24, 2015, the contents of the application is incorporated herein by reference in its entirety.

BACKGROUND OF THE INVENTION

1. Field of the Invention

The present disclosure relates to treatments for cancers. More particularly, the disclosure relates to treating cancer by use of novel double-stranded short interfering nucleic acid that inhibits the translation of Aurora-A mRNA.

2. Description of Related Art

Abnormal expression of Aurora-A and epidermal growth factor receptor (EGFR) have been observed in various types of cancer cells; and epidermal growth factor (EGF) is known to specifically increase the transcription of Aurora-A mRNA possibly via forming a transcription pre-initiation complex on the 5'-UTR region of Aurora-A mRNA; hence, the 5'-UTR region of Aurora-A has been hypothesized to be a potential target site for developing therapy to EGFR-associated cancers.

With the emerging use of post-transcriptional gene silencing technology, in particular, RNA interference (RNAi), as a tool to knock out expression of specific genes in a variety of organisms, it is now possible to map protein interactions in cell signaling pathway by systematically silencing functional genes, and thereby providing a new way of developing therapeutics for countless diseases. After extensive clinical researches and experiments, inventors of the present study have identified non-coding, short RNA molecules capable of suppressing Aurora-A gene expression via RNA interference, thus, these identified short RNA molecules are useful as a medicament for treating EGFR-mediated cancer to alleviate or minimize symptoms associated therewith in subjects in need of such treatment.

SUMMARY

The present disclosure is directed to novel double-stranded nucleic acid for treatment of, or prophylaxis against, cancer, particularly, EGFR-mediated cancer.

Accordingly, one aspect of the present invention is directed to an isolated double-stranded short interfering ribonucleic acid (siRNA) that inhibits the translation of Aurora-A mRNA via RNA interference, wherein (a) each strand of said siRNA molecule is about 17 to 21 ribonucleotides in length; and (b) one strand of said siRNA molecule comprises a ribonucleotide sequence having at least 90% sequence identity to any of SEQ ID NOs: 1, 2, 3, 4, 5, 6, 7, 8, 9, 10, 11, 12, 13 or 14.

According to one embodiment of the present disclosure, one strand of said siRNA molecule comprises at least one locked nucleic acid (LNA) molecules, 2'-sugar modification, modified internucleoside linkage or a combination thereof.

In another aspect, the present disclosure is directed to a method of treating a subject suffering from a cancer that is mediated through epidermal growth factor receptor (EGFR) signaling. The method comprises the step of administering to the subject a therapeutically effective amount of the siRNA molecule of this invention to counteract EGFR signaling mediated growth of cancerous cells by suppressing the translation of Aurora-A gene.

According to embodiments of the present disclosure, the siRNA molecule of this invention is a double-stranded siRNA that inhibits the translation of Aurora-A mRNA via RNA interference. Each strand of said siRNA molecule is about 17 to 21 ribonucleotides in length; and one strand of said siRNA molecule has a ribonucleotide sequence having at least 90% sequence identity to any of SEQ ID NOs: 3, 5 or 11.

According to embodiments of the present disclosure, one strand of the siRNA molecule comprises at least one LNA molecules, 2'-sugar modification, modified internucleoside linkage or a combination thereof. In one example, one strand of the siRNA molecule comprises 9 LNA molecules. In another example, one strand of the siRNA molecule comprises 10 LNA molecules.

According to embodiments of the present disclosure, the EGFR signaling mediated cancer may be colorectal cancer, liver cancer, breast cancer, or cervical cancer. In one preferred example, the subject is suffering from colorectal cancer.

In another aspect, the present disclosure is directed to a pharmaceutical composition for treating a cancer. The pharmaceutical composition comprises an effective amount of the siRNA molecule of this invention; and a pharmaceutically acceptable carrier.

In still another aspect, the present disclosure is directed to a method of treating a subject having cancer. The method includes steps of, administering to the subject the pharmaceutical composition of the present disclosure so as to suppress the growth of the cancer or ameliorate the symptoms associated with the cancer.

The details of one or more embodiments of the invention are set forth in the accompanying description below. Other features and advantages of the invention will be apparent from the detail descriptions, and from claims.

BRIEF DESCRIPTION OF THE DRAWINGS

These and other features, aspects and advantages of the present invention will become better understood with reference to the following description, appended claims and the accompanying drawings, where:

DESCRIPTION

Figure 1A:
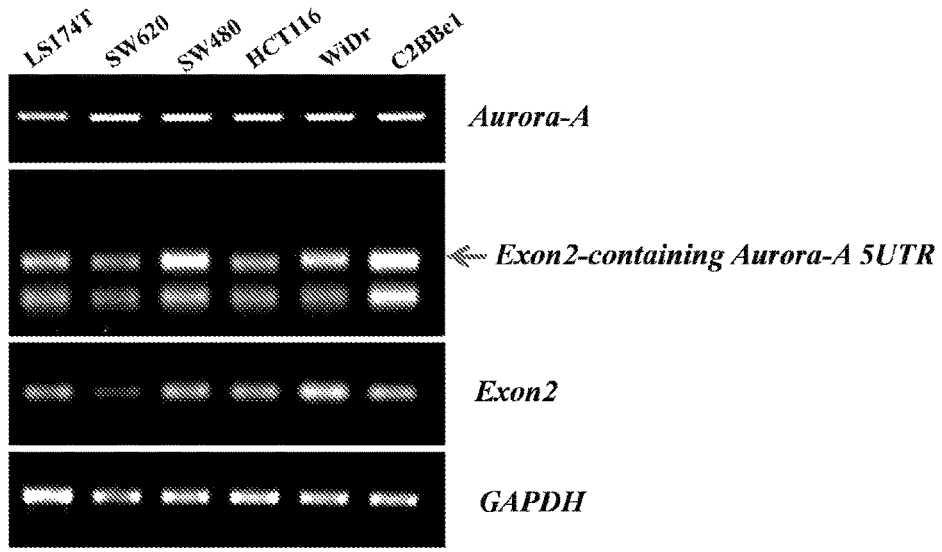
FIG. 1A illustrates the respective expression patterns of exon-2 containing Aurora-A 5'-UTR in various cell lines, including colorectal cancer cell line LS174T, hepatocarcinoma (HCC) cell lines Huh7 and HepG2, acute lymphoblastic leukemia (ALL) cancer cell line RS4; 11 and cervical cancer cell line HeLa in accordance with one embodiment of this invention.
Figure 1B:
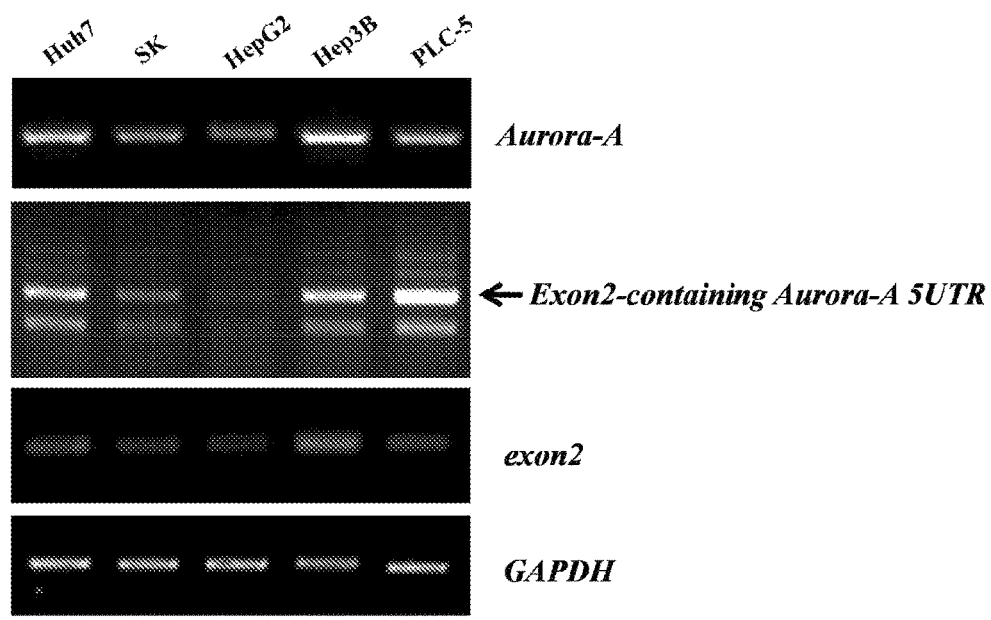
FIG. 1B illustrates the respective expression patterns of exon-2 containing Aurora-A 5'-UTR in various colorectal cancer cell lines including LS174T, SW620, SW480, HCT116, WiDr and C2BBel in accordance with one embodiment of this invention.
Figure 1C:
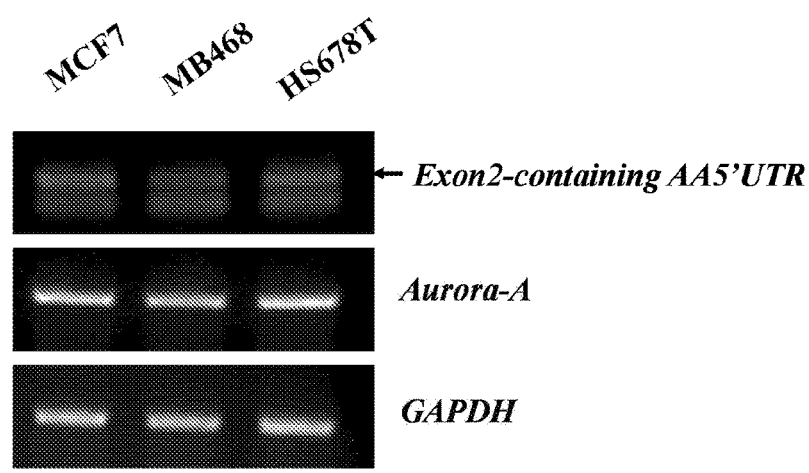
FIG. 1C illustrates the respective expression patterns of exon-2 containing Aurora-A 5'-UTR in various HCC cell lines including Huh7, SK, HepG2, and PL-5 in accordance with one embodiment of this invention.
Figure 1D:
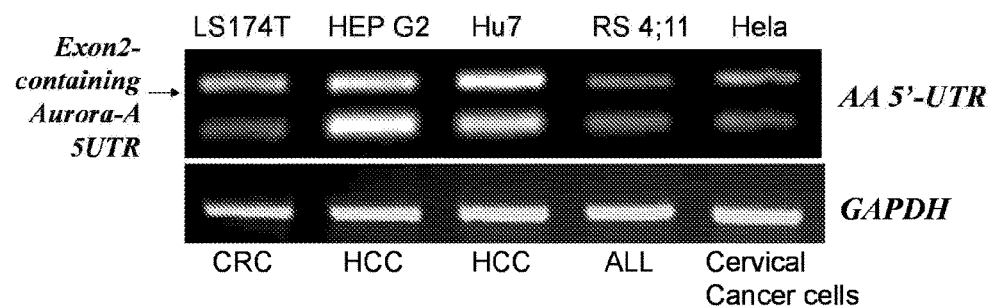
FIG. 1D illustrates the respective expression patterns of exon-2 containing Aurora-A 5'-UTR in various breast cell lines including MCF7, MB468, and HS678T in accordance with one embodiment of this invention.

The detailed description provided below in connection with the appended drawings is intended as a description of the present examples and is not intended to represent the only forms in which the present examples may be constructed or utilized. The description sets forth the functions of the invention and the sequence of steps for constructing and operating the examples. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

The term "nucleic acid" is defined as a molecule formed by covalent linkage of two or more nucleotides, which encompass DNA, RNA, and variants or analogues of such DNA or RNA. The terms "nucleic acid" and "polynucleotide" are used interchangeable herein.

As used herein, a "sequence" of a nucleic acid refers to the ordering of nucleotides which make up a nucleic acid. Throughout this application, nucleic acids are designated as having a 5' end and a 3' end. Unless specified otherwise, the left-hand end of a single-stranded nucleic acid is the 5' end; and the right-hand end of single-stranded nucleic acid is the 3' end.

The term "lock nucleic acid (LNA)" as used herein refers to a nucleic acid in which some nucleotides of the nucleic acid are lock nucleic acid monomers (i.e., bicyclic nucleotide or its analogues). The ribose moiety of an LNA nucleotide is modified with an extra bridge connecting the 2' oxygen and 4' carbon. The bridge "locks" the ribose in the 3'-endo (North) conformation, which is often found in the A-form duplexes. These LNA monomers are described inter alia in WO 2000/56746, WO 2001/25248, WO 2003/006475 and WO 2003/095467; disclosures of the respective recited publications are incorporated herein by reference.

The term "siLNA" is broadly used herein to refer the double-stranded LNA, thus a "siLNA" as used herein always comprises at least one LNA monomer.

The term "siRNA" refers to a double-stranded RNA. In a typical siRNA of this invention, the two strands usually have 17-21 nucleotides complementary to each other thereby creating a double strand. In siRNA, one strand is guiding and complementary to the target RNA (antisense strand), and the other strand (sense strand) has the same sequence as the target RNA and hence is complementary to the guiding/antisense strand.

"Percentage (%) sequence identity" with respect to any nucleotide sequence identified herein is defined as the percentage of nucleotide residues in a candidate sequence that are identical with the nucleotide residues in the specific nucleotide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two nucleotide sequences was carried out by computer program Blastn (nucleotide-nucleotide BLAST) provided online by Nation Center for Biotechnology Information (NCBI). The percentage sequence identity of a given nucleotide sequence A to a given nucleotide sequence B (which can alternatively be phrased as a given nucleotide sequence A that has a certain % nucleotide sequence identity to a given nucleotide sequence B) is calculated by the formula as follows:

$$\frac{X}{Y} \times 100\%$$

where X is the number of nucleotide residues scored as identical matches by the sequence alignment program BLAST in that program's alignment of A and B, and where Y is the total number of nucleotide residues in A or B, whichever is shorter.

As used herein, the terms "treat" or "treating" or "treatment" refer to preventative (e.g., prophylactic), curative or palliative treatment. The term "treating" as used herein refers to application or administration of the siRNA of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable.

The term "effective amount" as used herein refers to the quantity of a component which is sufficient to yield a desired response. The term "therapeutically effective amount" as used herein refers to the amount of therapeutically agent (e.g., the present siRNA or siLNA) to result in a desired "effective treatment" as defined hereinabove. The specific therapeutically effective amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed. A therapeutically effective amount is also one in which any toxic or detrimental effects of the compound or composition are outweighed by the therapeutically beneficial effects.

The term "subject" or "patient" as used herein refers to a human or a non-human animal that is diagnosed with tumor or cancer (solid or metastatic cancer) and subject to methods of the present invention. The term "subject" or "patient" intended to refer to both the male and female gender unless one gender is specifically indicated. Examples of a non-human animal include all vertebrates, e.g., mammals, such as primates, dogs, rodents (e.g., mouse or rat), cats, sheep, horses or pigs; and non-mammals, such as birds, amphibians, reptiles and etc.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

2. The Present siRNAs and siLNAs

The present disclosure is directed to a novel solution for treating cancer such as colorectal cancer, by use of short interfering ribonucleic acid (siRNA) molecules. Accordingly, in its broadest aspect, the present invention relates to a double-stranded nucleic acid comprises two ribonucleotide sequences complementary to at least a portion of a target mRNA such as Aurora-A mRNA, and is capable of resulting in suppressing the expressed target mRNA via RNA interference mechanism. The siRNA molecule of this invention comprises two strands of ribonucleic acid, wherein (a) each strand of said siRNA molecule is about 17 to 21 ribonucleotides in length; and (b) one strand of said siRNA molecule comprises a ribonucleotide sequence having at least 90% sequence identity to any of SEQ ID NOs: 1, 2, 3, 4, 5, 6, 7, 8, 9, 10, 11, 12, 13 or 14.

Each strand of the double-stranded siRNA of the invention may be 17 to 21 ribonucleotides in length, such as 17, 18, 19, 20, or 21 ribonucleotides in length. In one preferred example, each strand of the siRNA of the invention has 17 ribonucleotides in length. In another preferred example, each strand of the siRNA of the invention has 18 ribonucleotides in length. In still another preferred example, each strand of the siRNA of the invention has 21 ribonucleotides in length. The double-stranded siRNA of the invention may be composed of entirely RNA molecules or it may be composed of RNA molecules in combination with at least one LNA molecules, such as 2'-O—, 4'-C methylene bicyclonucleoside monomer. In general, the individual strand of the double-stranded nucleic acid (siRNA or siLNA) of this invention may contain at least about 5%, 10%, 15%, or 20% LNA monomers, based on total number of nucleotides in the strand. In certain embodiments, the double-stranded nucleic acid (siRNA or siLNA) of this invention will contain at least about 25%, 30%, 40%, 50% or 60% LNA monomers, based on total number of nucleotides in the strand; preferably about 40% LNA monomers; and more preferably about 60% LNA monomers. In one embodiment of this invention, the double-stranded nucleic acid of this invention is composed of entirely RNA molecules, in which one strand comprises a ribonucleotide sequence having at least 90% sequence identity, such as 90%, 91%, 92%, 93%, 94%, 95%, 96%, 97%, 98%, 99% or 100%, to any of SEQ ID NOs: 1, 2, 3, 4, 5, 6, 7, 8, 9, 10, 11, 12, 13 or 14. In another embodiment of this invention, the double-stranded nucleic acid of this invention is composed of RNA molecules in combination with LNA molecules, in which one strand is composed of entirely RNA molecules, and the other strand is composed of RNA molecules in combination with at least about 50% or 60% LNA molecules. Alternatively, the double-stranded siRNA may comprise other modification, such as 2'-sugar modification, modified internucleoside linkage or a combination thereof.

In one embodiment of this invention, the sense strand of the double-stranded nucleic acid comprises at least one LNA monomer. For example, the sense strand of the double-stranded nucleic acid comprises 9 LNA monomers, and the anti-sense strand comprises none of the LNA monomers. In another embodiment, the sense strand of the double-stranded nucleic acid comprises 10 LNA monomers, and the anti-sense strand comprises none of the LNA monomer. In a further embodiment of this invention, the sense strand of the double-stranded nucleic acid comprises at least one LNA monomer, and the antisense strand comprises at least one LNA monomer. For example, the sense strand comprises two LNA monomers, and the antisense strand comprises one LNA monomer.

One advantage of having LNA monomer(s) in a nucleic acid is that the stability of nucleic acid is improved; accordingly, the siRNA or siLNA of this invention may include the incorporation of LNA monomers into a standard RNA oligonucleotide to increase the stability of the resulting siRNA or siLNA molecule, such as increasing the resistance of siRNA or siLNA toward protease (endonucleases and exonucleases) and thereby increasing its circulating half-life in a biological sample.

Currently, there are various ways for generating siRNAs for gene silencing studies, including chemical synthesis, in vitro transcription, digestion of long dsRNA by an RNase III family enzyme, expression in cells from an siRNA expression plasmid or viral vector, and expression in cells from a real time polymerase chain reaction (RT-PCR)-derived siRNA expression cassette. The first three methods involve in vitro preparation of siRNAs that are then introduced directly into cells by lipofection, electroporation or other technique. The last two methods rely on the introduction of DNA-based vectors and cassettes that express siRNA within the cells.

The siRNA molecules of this invention were obtained by in vitro preparation and/or chemical synthesis using protocols known in the art. For example, the double-stranded nucleic acid of this invention may be produced using the polymeriszation techniques of nucleic acid chemistry, which is well known to a person of ordinary skill in the art of organic chemistry. In general, standard oligomerisation cycles of the phosphoramidite approach may be used, but other chemistries, such as H-phosphonate chemistry or phosphotriester chemistry may also be used. Alternatively, the siRNA molecules may be cloned by RT-PCR expression cassette, by putting into an appropriate vector and delivering into a cell for expression. Once expressed, the siRNA molecules interact with the target mRNA and generate an interference RNA response. The siRNA molecules may comprise a delivery vehicle such as liposomes for administration to a subject, carriers, and diluents and/or can be present in pharmaceutically acceptable formulations. Methods for delivering nucleic acid molecules are well known in this art, including, but are not limited to, encapsulation in liposomes, iontophoresis, or by incorporation into other vesicles, such as biodegradable polymers, hydrogel, cyclodextrins, or by proteinaceous vectors.

All siRNA oligonucleotides used in this invention are listed in Table 1. The siLNAs of this invention were obtained by modifying the corresponding siRNA as listed in Table 1 with at least one LNA molecules, such as 2'-O—, 4'-C methylene bicyclonucleoside monomer. Table 2 lists the siLNA oligonucleotides prepared from three siRNAs listed in Table 1, namely, siRNA oligonucleotides respectively having sequence ID NO: 5, 11 and 13, in which the LNA molecules are indicated in upper case letters.

TABLE 1

Sequences of siRNA of this invention

| Name | Sequence | SEQ ID NO |
|---|---|---|
| AA5UTR siRNA-1 (31-49)* | 5'-uuu cuu auc aaa uau ccc cuu-3' (sense) | 1 |
|  | 5'-ggg gau auu uga uaa gaa auu-3' (anti-sense) | 2 |
| AA5UTR siRNA-2 (81-99)* | 5'-aaa aug cug gga uua cgg guu-3' (sense) | 3 |
|  | 5'-ccc gua auc cca gca uuu uuu-3' (anti-sense) | 4 |
| New-AA5UTR siRNA-2 (83-99)* | 5'-aaa aug cug gga uua cg-3' (sense) | 5 |
|  | 5'-cgu aau ccc agc auu uu-3' (anti-sense) | 6 |
| AA5UTR siRNA-3 (33-51)* | 5'-agu uuc uua uca aau auc cuu-3' (sense) | 7 |
|  | 5'-gga uau uug aua aga aac uuu-3' (anti-sense) | 8 |
| AA5UTR siRNA-4 (83-101)* | 5'-cga aaa ugc ugg gau uac guu-3' (sense) | 9 |
|  | 5'-cgu aau ccc agc auu uuc guu-3' (anti-sense) | 10 |
| AA5UTR siRNA-5 (26-43)* | 5'-auc aaa uau ccc cgc acu-3' (sense) | 11 |
|  | 5'-agu gcg ggg aua uuu gau-3' (antisense) | 12 |
| AA5UTR siRNA-6 (85-102)* | 5'-ccg aaa aug cug gga uua-3' (sense) | 13 |
|  | 5'-uaa ucc cag cau uuu cgg-3' (anti-sense) | 14 |

*numbers in the parenthesis indicate the ribonucleotide positions in exon 2 mRNA sequence, which comprises total of 110 ribonucleotides.

TABLE 2

Sequence of three exemplified siLNAs of this Invention

| Name | Sequence | SEQ ID NO |
|---|---|---|
| New-AA5UTR siLNA-2 (83-99)* | 5'-AAA AUg cug gga UUA CG-3' (sense) | 5 |
|  | 5'-cgu aau ccc agc auu uu-3' (anti-sense) | 6 |
| AA5UTR siLNA-5 (26-43)* | 5'-AUC Aaa uau ccc cGC ACU-3' (sense) | 11 |
|  | 5'-agu gcg ggg aua uuu gau-3' (antisense) | 12 |

TABLE 2-continued

Sequence of three exemplified siLNAs of this Invention

| Name | Sequence | | SEQ ID NO |
|---|---|---|---|
| AA5UTR siLNA-6 (85-102)* | 5'-CCG Aaa aug cug gGA UUA-3'<br>5'-uaa ucc cag cau uuu cgg-3' | (sense)<br>(anti-sense) | 13<br>14 |

LNA, upper case; and RNA, lower case.

Accordingly, a further aspect of this invention relates to the use of the double-stranded nucleic acid of this invention for the manufacture of a medicament for the treatment of cancer.

Accordingly, a pharmaceutical composition for treatment of, or prophylaxis against, cancer is provided. The pharmaceutical composition comprises at least one double-stranded nucleic acid of this invention as an active ingredient; and a pharmaceutically acceptable carrier. Optionally, the pharmaceutical composition may further comprise another anti-cancer agent, such as a chemotherapeutic agent, an anti-inflammatory agent, or an immune-modulating agent.

The nucleic acid of this invention may be suspended in a suitable dispersion medium, such as water, PBS, saline, oils, or fatty acids. The pharmaceutical compositions thus prepared may be administered parenterally, by inhalation spray, topically, rectally, nasally, buccally or vaginally. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the composition is administered intramuscularly, intraperitoneally or intravenously, and most preferably, the composition is administered intramuscularly. In one example, the composition of this invention is injected intramuscularly from a site on one limb (i.e., arm or leg) of the subject. The body portion suitable for injection is selected based on the followings, such as the choice of the nucleic acid to be released, the subject's personal condition including sex, age, body weight, and/or current and prior medical conditions. An experienced physician may determine suitable body portion for injection without undue experiment. Sterile injectable forms of the composition of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, phosphate buffer solution and isotonic sodium chloride solution (i.e., saline). In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The dosage required depends on the choice of the route of administration; the nature of the formulation; the nature of the subject's illness; the subject's weight, surface area, age and sex; other drugs being administered; and the judgement of the attending physician. Suitable dosages are from 0.15 mg to 1.5 mg nucleic acid/Kg of body weight, such as 0.15, 0.2, 0.3, 0.4, 0.5, 0.6, 0.7, 0.8, 0.9, 1.0, 1.1, 1.2, 1.3, 1.4, and 1.5 mg nucleic acid/Kg of body weight; preferably from 0.3 mg to 1.2 mg nucleic acid/Kg of body weight, such as 0.3, 0.4, 0.5, 0.6, 0.7, 0.8, 0.9, 1.0, 1.1, and 1.2 mg nucleic acid/Kg of body weight; and more preferably from 0.5 mg to 1.0 mg nucleic acid/Kg of body weight, such as 0.5, 0.6, 0.7, 0.8, 0.9, and 1.0 mg nucleic acid/Kg of body weight. Variations in the needed dosage are to be expected in view of the variety of angiogenesis inhibitors available and the different efficiencies of various routes for administration. Those of skill in the art can readily evaluate relevant factors and based on this information, determine the particular dosage to be used for an intended purpose.

This invention also features methods for treating a subject pre-diagnosed with a tumor or a cancer, said method comprising administering the double-stranded nucleic acid of this invention or the composition of this invention to a subject in need thereof; and further comprising administering additional medicament (e.g., a chemotherapy or radiotherapy) to the subject. A subject herein refers to a human and a non-human animal. In a preferred example, the subject is a human. Examples of the tumor or cancer suitable for receiving treatment of the present invention include, but are not limited to, colon cancer, colorectal cancer, breast cancer, prostate cancer, hepatocellular carcinoma, melanoma, glioblastoma, brain tumor, hematopoeitic malignancies, retinoblastoma, renal cell carcinoma, head and neck cancer, cervical cancer, esophageal cancer, and squama cell carcinoma. In one example, the subject has been diagnosed with a colorectal cancer. In another example, the subject has been diagnosed with a hepatocellular carcinoma (HCC). In still another example, the subject has been diagnosed with a breast cancer. The subject may have received medical treatment before being subject to the method and/or composition of this invention. The medical treatment herein refers to surgery, chemotherapy or radiotherapy commonly applied to a patient with tumor. Therefore, to augment the antitumor effects of gene therapy, the subject pre-diagnosed with tumor may also receive other anti-tumor therapy before, at the same time or after subjecting to methods and/or compositions of this invention. In one example, the subject is treated with chemotherapy or radiotherapy before receiving the method and/or composition of this invention.

The following Examples are provided to illustrate certain aspects of the present invention and to aid those of skilled in the art in practicing this invention. These Examples are in no way to be considered to limit the scope of the invention in any manner.

EXAMPLES

Materials and Methods

Cell Culture

Various cell lines including colorectal cancer cell lines (e.g., LS174T, SW620, SW480, HCT116, WiDr and C2BBe1), colon cancer cell line WiDR, normal colon cell line (i.e., CRL-1790), hepatocellular carcinoma (HCC) cell lines (e.g., Huh7, SK, HepG2, Hep3B, and PLC-5), breast cancer cell lines (e.g., MCF7, MB468, and HS678T), and cervical cancer cell line (e.g., HeLa) were used in this study. In general, cells were cultured in their respective suitable mediums that were supplemented with 10% fetal bovine serum (FBS), 100 µg/ml streptomycin and 100 U/ml penicillin; and maintained at 37° C. in an environment containing 95% $CO_2$. Specifically, LS174 cells were cultured in minimum essential medium (MEM-GIBCO, Invitrogen, Carlsbad, Calif., USA); SW480 and SW620 cells were cultured in Leibovitz's L-15 medium (L-15, GIBCO); HCT116 and MB468 cells were cultured in RPMI medium 1640; HeLa, Huh7, SK, HepG2, Hep3B, PLC-5, C2BBe1, and CRL-1790 were cultured in Dulbecco's Modified Eagle's medium (Sigma, D5648); WiDr and MCF7 were cultured in ATCC-formulated Eagle's Minimum Essential Medium (No. 30-2003).

Construction of Murine Aurora-A siRNAs or siLNAs

The human Aurora-A mRNA 5'-UTR were used as the target sequence for the preparation of Aurora-A siRNAs. Specifically, AA5UTR siRNA-1, siRNA-2, new siRNA-2, siRNA-3, siRNA-4, siRNA-5, and siRNA-6 of this invention were prepared using target sequence at positions 384 to 402, 434 to 452, 436 to 452, 385 to 404, 436 to 454, 379 to 396, and 438 to 455, respectively. Negative control siRNA (commercial kit provided from Dharmacon, Thermo, Lafayette, Colo., USA) were synthesized by PCR-derived siRNA expression cassettes according to the manufacturer's instructions (Dharmacon).

LNA has been reported to increase the siRNA potency without perturbing the overall helical structure of siRNA, hence LNA-modified siRNA (hereafter termed siLNA), and namely the siLNAs derived from the siRNAs as indicated in the above Table 1, were synthesized in 1 nmol scale on a MOSS Expedite instrument platform accordance with the procedures described in the instrument manual.

The murine Aurora-A mRNA 5'-UTR siRNAs and siLNAs were then cloned into pGL3 vector, which contains a SV40 promotor and a luciferase reporter. The plasmids were constructed by ligation of double-stranded DNA oligonucleotide corresponding to the target sequence in the pGL3-plasmid. The sense and anti-sense direction of the insert was confirmed after ligation by PCR and sequencing.

Transfecting Cells with the Murine Aurora-A siRNA or siLNA Constructs

Various cell lines, including colorectal cancer cell lines (e.g., LS174T, SW620, SW480, HCT116, WiDr and C2BBe1), hepatocellular carcinoma (HCC) cell lines (e.g., Huh7, SK, HepG2, Hep3B, and PLC-5), breast cancer cell lines (e.g., MCF7, MB468, and HS678T), and cervical cancer cell line (e.g., HeLa) were respectively maintained and cultured on 6-well plates, and were transfected with the plasmids containing either siRNAs or siLNAs described above with the aid of the Lipofectamine 2000 (Invitrogen, Carlsbad, Calif. USA). Specifically, 0.5 µg/well pGL3 plasmid contained human Aurora-A mRNA 5'-UTR siRNA or siLNA and 6 µl/well Lipofectamine 2000 were allowed to form complexes in a period of 25 min at room temperature in antibiotic-free DMEM medium. The complexes were then added to cells maintained and cultured in 6-well dishes and further incubated for another 24 hrs. The transfection of human Aurora-A mRNA 5'-UTR siRNA or siLNA in cells was confirmed by the detection of human Aurora-A mRNA 5'-UTR gene expression either in RNA level by Quantitative Real Time PCR (Q-PCR or RT-PCR) analysis or in protein level by ELSA assay.

Quantitative RT-PCR

Total RNA of cells transfected with human Aurora-A mRNA 5'-UTR siRNAs as described above was isolated using TriSure reagent according to the manufacturer's instructions (Bioline USA Inc, Taunton, Mass.). An amount of 400-800 ng of DNase-treated total RNA was used as template for first strand DNA synthesis according to the manufacturer's protocol (Applied Biosystem, Stockholm, Sweden). An aliquot of the cDNA reaction were analyzed by Quantative Real-Time PCR by ABI PRISM 7000 (Applied Biosystem, Grand island, NY). Gene-specific primers and probes for target genes (i.e., Aurora-A mRNA 5'-UTR, Aurora-A, Aurora-A mRNA Exon2 or GAPDH) were mixed separately with TaqMan Universal Mastermix (Applied Biosystem, Grand Island, N.Y.) and added to the cDNA to be analyzed. Samples were run in triplicate and the data obtained were analyzed with ABI PRISM SDS Software (Applied Biosystem).

Immunoblot Assay

Cells were harvested from cultured dishes by a lysing buffer (50 mM Tris-HCl, 150 mM NaCl, 0.5% sodium deoxycholate, 1 mM EDTA, and 2 mM EGTA) containing 1 mM sodium orthovanadate, 1 mM phenylmethylsulfonyl fluoride, 10 µg/ml leupetin and 10 µg/ml aprotinin. The lysate were centrifuged at 12,000×g for 5 min at 4° C. The supernatants were collected and stored at −70° C. until used. The immunoprecipitation complexes were resolved by SDS-PAGE and subject to immunoblotting analysis using antibodies directed to Aurora-A, GAPDH, pro-caspase 3, caspase 3, and tubulin.

In Vivo Transcription Assay

The in vivo transcription assay was performed in accordance with the method described previously by Yeh et al (*Mol Biol Cell* 2008; 19:3812-3822). Briefly, SW480 cells were transfected with various concentrations of siRNAs, siLNAs of this invention, or other Aurora-A 5'-UTR isoforms (e.g., exon2+, and exon2-) containing luciferase reporter gene constructs. Luciferase activities were measured using Luciferase Reporter Assay protocol (Promega) according to the manufacturer's instruction.

Cytotoxicity Assay

Cytotoxity induced by siRNAs and/or siLNAs of this invention was conducted on normal colon cells (CRL-1790) as well as cancerous cells including colorectal cancer cell line SW480, and HeLa cells. Briefly, cells were transfected with various concentrations of siRNA or siLNA (i.e., 0, 0.1, 0.5, 1, 2, 5, 10, 20, 50, or 100 nM) of this invention using Lipofectamine 2000 for 48 hours. The cytotoxicity was then quantified by immunoblot assay as described above, in which tubulin was used as a loading control.

Cell Proliferation Assay

Proliferation of the cells were evaluated by use of the Cell Counting Kit-8 (CCK-8), which is a sensitive colorimetric assay for the determination of the number of viable cells in the proliferation and cytotoxicity assays. WST-8 (2-(2-methoxy-4-nitrophenyl)-3-(4-nitrophenyl)-5-(2,4-disulfophenyl)-2H-tetrazolium, monosodium salt) in the CCK-8 kit is bioreduced by cellular dehydrogenases to an orange water-soluble formazan dye in the presence of an electron carrier, 1-Methoxy PMS. The amount of formazan produced is directly proportional to the number of living cells. Briefly, cells were treated with the siRNAs or siLNAs of the present disclosure (10 nM) for 1-4 days, then CCK-8 solution was added directly to the cells, the reduction was allowed to proceed for at least 4 hrs before the addition of 500 µL isopropanol. Absorbance at 450 nm was then measured.

In Situ Cancer Induction and In Vivo Cancer Treatment

NOD-SCID mice (each was about 5-6 weeks old) were used in the present study. The mice were kept at pathogen-free environment with temperature and relative humidity (RH) respectively set at 22±3° C. and 50±20%, and light/dark cycle of 12 hrs. Food and water were available ad libitum. All procedures involving animal research complied with the guidelines approved by the Chinese Taipei Society of Laboratory Animal Sciences.

Animals were assigned to respective groups based on their body weights. On the day of experiments, animals in the test groups were subcutaneously injected with 1×10$^6$ SW480 cells into the left flank, whereas animals in the control group were injected with buffer solution. The tumor was allowed to grow to about 50 mm$^3$ in size, then the test animals were randomly assigned into 3 groups, and respectively treated with carriers, control siLNA or siLNA-2, twice per week. Body weight and tumor size were also measured twice per week. Animals were sacrificed on day 16, and tumors were excised and weighted, and the size was calculated in accordance with the equation of: length×(width)$^2$×0.5.

Example 1 Exon-2-Containing Aurora-A 5'-UTR is Universally Expressed in Various Types of Cancer Cell Lines There are 6 different isoforms of the 5'-UTR region of Aurora-A mRNA, which are exons 1, 2 and 3, in which exon 1 has 3 variants (i.e., exons 1, 1a, and 1b) and exon 2 has 2 variants (i.e., exons 2 and 2a). Previous studies indicated that the expression of exon 2 of the Aurora-A mRNA 5'-UTR in cancer cells increases with treatment of EGF (*J Cell Mol Med.* 2010, 14:1520-1531); hence, in this example, the universal expressions of exon 2 of Aurora-A mRNA 5'-UTR in different types of cancer cells were investigated.

Various types of cancer cell lines including colorectal cancer cell lines (e.g., LS174T, SW620, SW480, HCT116, WiDr and C2BBe1), hepatocellular carcinoma (HCC) cell lines (e.g., Huh7, SK, HepG2, Hep3B, and PLC-5), breast cancer cell lines (e.g., MCF7, MB468, and HS678T), and cervical cancer cell line (e.g., HeLa) were used in this example. Cancer cells were cultured and maintained in accordance with the procedures described in the section of "Material and Methods." The intrinsic expressions of exon 2, Aurora-A, exon 2 containing Aurora-A mRNA 5'-UTR, as well as glyceraldehyde-3-phosphate dehydrogenase (GAPDH, which served as a house-keeping gene) were measured by immunoblot assay, and the results are respectively depicted in FIGS. 1A to 1D.

The results illustrated in FIG. 1 confirmed that most cancer cell lines that were tested expressed Aurora-A 5UTR isoforms, including exon-2 containing Aurora-A 5 UTR and its variant.

Example 2 Correlation Between Expression Pattern of Aurora-A Exon-2 and Aurora-A in Colorectal Cancer Patients One hundred and fifty-five cases of human colorectal cancer tissues with different Modified Astler-Coller (MAC) staging were collected, and the expression of Aurora-A and Aurora-A exon2 in the collected tissues were analyzed. Briefly, total mRNAs were isolated from human colorectal cancer tissues, and the expression of Aurora-A and Aurora-A 5'-UTR exon2 were analyzed by RT-PCR, and the expression levels were normalized with relevant to that of GAPDH. The results are summarized in Table 3.

TABLE 3

Number of Incidences of the expression of Aurora-A exon-2 with Aurora-A in human colorectal cancer tissues

| CRC tissues | Aurora-A+ | Aurora-A− | Total (N) |
|---|---|---|---|
| exon 2+ | 88* | 8 | 96 |
| exon 2− | 26 | 33 | 59 |
| Total (N) | 114 | 41 | 155 |

*Chi square analysis, p < 0.0001

As indicated in Table 3, the expression of exon2 is positively correlated with Aurora-A in human colorectal tissue.

Example 3 Inhibition of the Transcription of Exon-2 Containing Aurora-A mRNA 5'-UTR by siRNAs or siLNAs Colorectal cancer SW480 cell line was treated with siRNA-2 or LNA modified siRNA-2 (i.e., siLNA-2), then the expression of exon1, and exon2-containing Aurora-A mRNA 5'-UTR were respectively measured by RT-PCR and immunoblot assay. Results are illustrated in FIGS. 2A and 2B.

Figure 2:
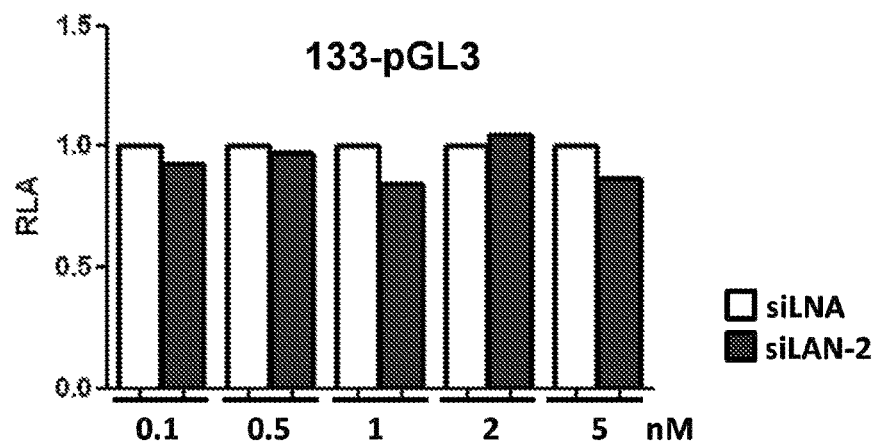
FIG. 2 illustrate the respective inhibition of the transcription of (A) exon1; and (B) exon1 and exon2-containing Aurora-A mRNA via control scramble siLNA and the present siLNA-2 analyzed by Q-PCR in accordance with one embodiment of this invention.
Figure 2:
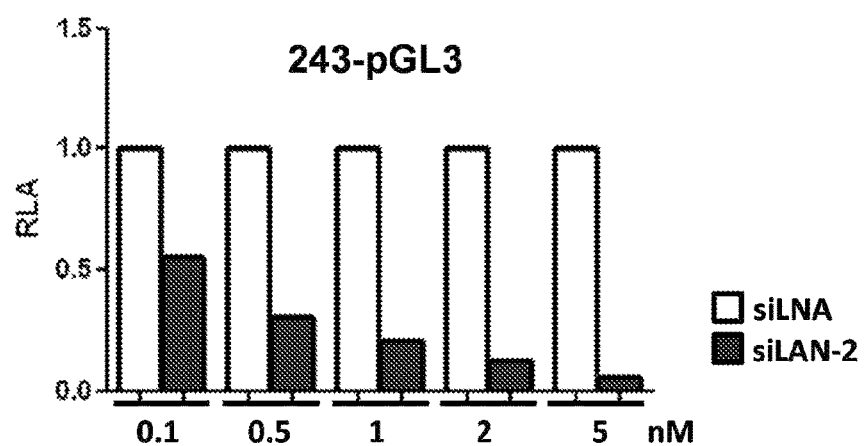

According to FIG. 2, while the transcription of exon 1 containing Aurora-A mRNA was not significantly affected by the scrambled siLNA or the present siLNA-2, yet the suppression of the transcription of exon 2 containing Aurora-A mRNA was enhanced by having LNA nucleotides in the present siRNA (i.e., siLNA-2) in a dose-dependent manner.

Example 4 siLNA-2 Reduced Viability of Cancer Cells and Suppressed the Proliferation of Cancer Cells In this example, the ability of siLNA-2 in killing colon rectal cancer cells (e.g., SW480 and HTC116 cells) were assessed by measuring the activity of capase-3/7 in accordance with procedures described in "Materials and Methods." Results are depicted in FIG. 3.

Figure 3A:
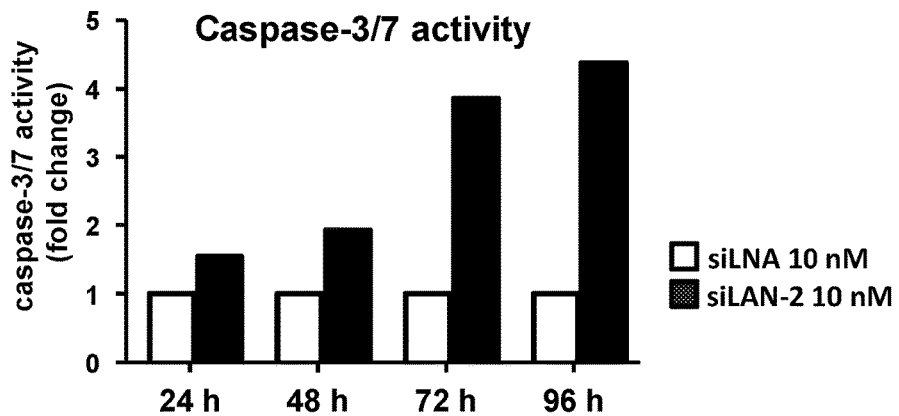
FIG. 3A illustrates the effect of the present siLNA-2 in inducing the death of colorectal cancer cells in accordance with one embodiment of this invention.
Figure 3B:
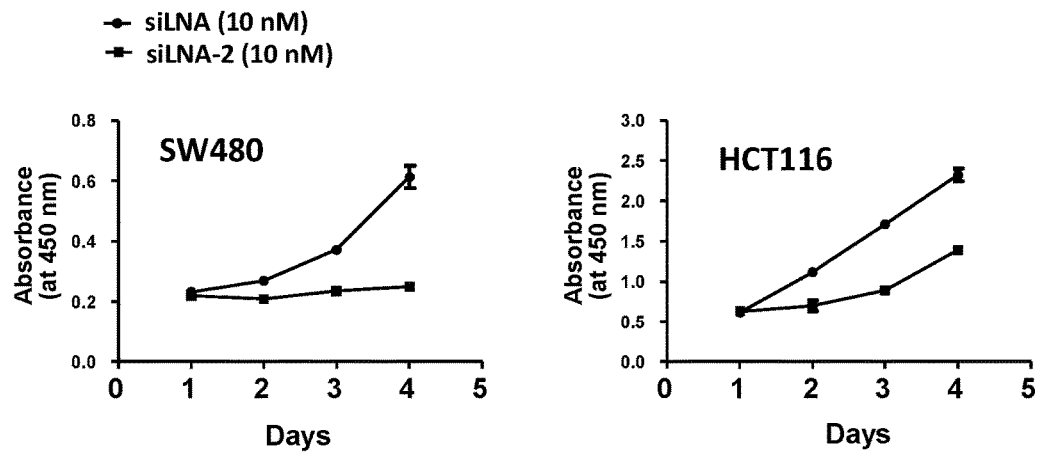
FIG. 3B illustrates the effect of the present siLNA-2 in suppressing the proliferation of SW480 or HCT116 in accordance with one embodiment of this invention.
Figure 3C:
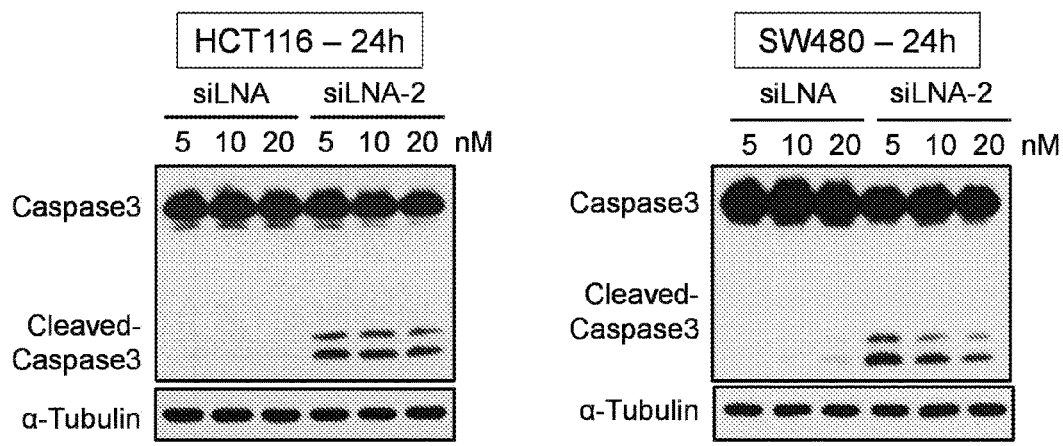
FIG. 3C illustrates the effect of the present siLNA-2 on caspase 3 activity in SW480 or HCT116 in accordance with one embodiment of this invention.

As illustrated in FIG. 3A, the capase-3/7 activity increased with an increase in the treatment time, by 72 hrs, the measured capase-3/7 activity in the treatment group was about 4 folds of that of the control group, which is an indicative of massive cell death. This observation that siLNA-2 possessed the ability of inducing cancer cell death was also confirmed by use of cell proliferation assay, as depicted in FIG. 3B. The proliferation of cancer cells (e.g., SW480 and HTC116 cells) treated with 10 nM siLNA-2 was significantly suppressed, as compared with that of un-treated cancer cells. The cleaved Caspase 3 was detected in HCT116 cells and SW480 cells after 24 h siLNA-2 treatment (FIG. 3C). Further, the $IC_{50}$ of siLNA-2 in suppressing the proliferation of SW480, HCT-116, and Huh7 cancer cells were about 2.048, 15.285 and 11.51 nM, respectively (data not shown).

Figure 4:
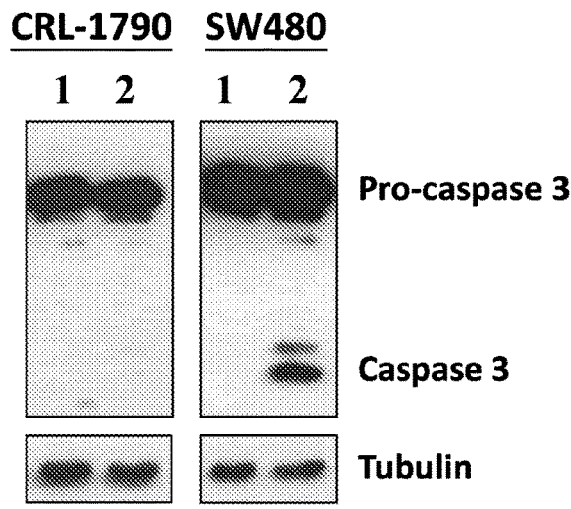
FIG. 4 illustrates the effect of the present siLNA-2 on the normal colorectal cell CRL-1790 in accordance with one embodiment of this invention.

In addition, though siLNA-2 of the present disclosure may induce cancer cell death and/or suppress its proliferation, yet it does not affect the growth of normal healthy cells. As illustrated in FIG. 4, the capase-3/7 activity of the normal colorectal cell CRL-1790 was not affected by the treatment of siLNA-2, which indicated that siLNA-2 of the present disclosure possessed no cytotoxicity toward normal colorectal cells.

Example 5 siLNAs Inhibit Xenografted Tumor Growth

Xenografted tumor was created on test animals in accordance with the procedures described in the section of "Materials and Methods." The animals were then treated with siRNA and/or siLNA of the present disclosure. Results are illustrated in FIG. 5.

Figure 5A:
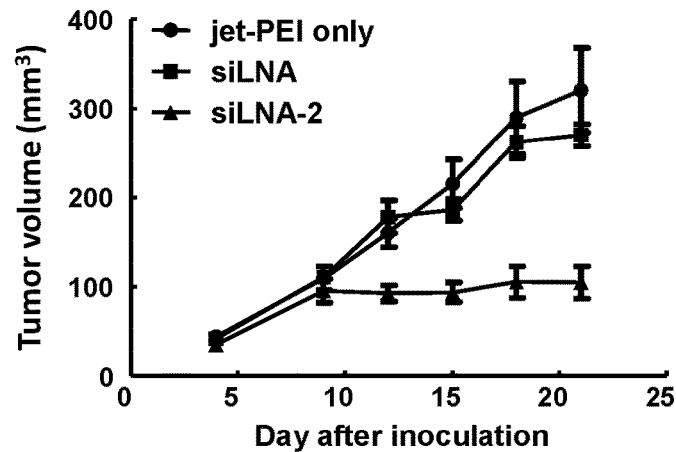
FIG. 5A illustrates the effect of siLNA-2 in suppressing the growth of the xenografted tumor in accordance with one embodiment of this invention.
Figure 5B:
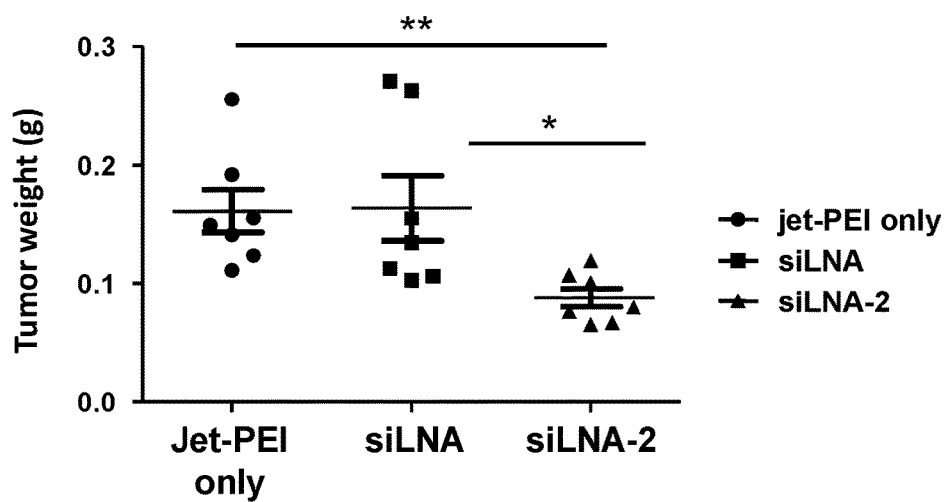
FIG. 5B illustrates the effect of siLNA-2 on the body weight of an animal bearing xenografted tumor thereon in accordance with one embodiment of this invention.
Figure 5C:
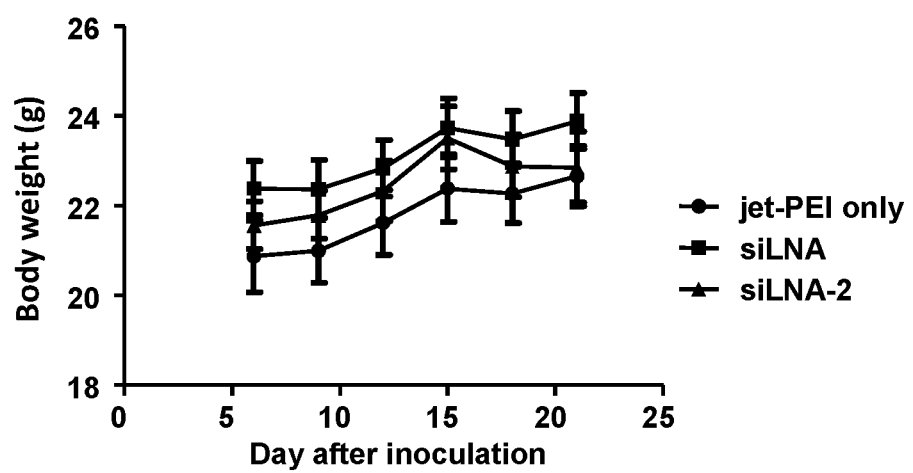

FIG. 5A is a line graph depicting the changes in tumor size with or without being treated with the siLNA of the present disclosure. The data clearly indicates that in the case when the animals were treated with siLNA of the present disclosure, the tumor size (FIG. 5B) was much smaller as compared with that of the control, in which the size of the tumor increased with time. Further, the treatment of scrambled siLNA did not result in significant body weight changes (FIG. 5C).

Taken together, findings in this invention support the proposition that EGFR-mediated cancerous growth, such as the growth of colorectal cancer cells, may be treated by introducing interference RNA, particularly siRNA that interferes with the expression of exon2 containing Aurora-A 5'UTR mRNA, into a subject (e.g., a human patient) in need of such treatment.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a subject suffering from a cancer that is mediated through epidermal growth factor receptor (EGFR) signaling, comprising administering to the subject a therapeutically effective amount of an siRNA molecule to counteract EGFR signaling mediated growth of cancerous cells by inhibiting the translation of Aurora-A mRNA, wherein (a) each strand of said siRNA molecule is about 17 to 21 ribonucleotides in length; and (b) one strand of said siRNA molecule comprises a ribonucleotide sequence having at least 90% sequence identity to any of SEQ ID NOs: 1, 2, 3, 4, 5, 6, 7, 8, 9, 10, 11, 12, 13 or 14.

2. The method of claim 1, wherein one strand of said siRNA molecule comprises a ribonucleotide sequence of SEQ ID NOs: 3, 5, or 11.

3. The method of claim 1, wherein the cancer is colorectal cancer, liver cancer, breast cancer, or cervical cancer.

4. The method of claim 1, wherein one strand of said siRNA molecule comprises at least one LNA molecules.

5. The method of claim 4, wherein one strand of said siRNA molecule comprises 10 LNA molecules.

6. The method of claim 1, wherein the subject is human.

* * * * *

SEQUENCE LISTING

```
<160> NUMBER OF SEQ ID NOS: 14

<210> SEQ ID NO 1
<211> LENGTH: 21
<212> TYPE: RNA
<213> ORGANISM: Artificial Sequence
<220> FEATURE:
<223> OTHER INFORMATION: siRNA_sense

<400> SEQUENCE: 1
uuucuuauca aauaucccu u                                              21

<210> SEQ ID NO 2
<211> LENGTH: 21
<212> TYPE: RNA
<213> ORGANISM: Artificial Sequence
<220> FEATURE:
<223> OTHER INFORMATION: siRNA_anti-sense

<400> SEQUENCE: 2
ggggauauuu gauaagaaau u                                             21

<210> SEQ ID NO 3
<211> LENGTH: 21
<212> TYPE: RNA
<213> ORGANISM: Artificial Sequence
<220> FEATURE:
<223> OTHER INFORMATION: siRNA_sense

<400> SEQUENCE: 3
aaaaugcugg gauuacgggu u                                             21

<210> SEQ ID NO 4
<211> LENGTH: 21
<212> TYPE: RNA
<213> ORGANISM: Artificial Sequence
<220> FEATURE:
<223> OTHER INFORMATION: siRNA_anti-sense

<400> SEQUENCE: 4
```

-continued cccguaaucc cagcauuuuu u                                    21

<210> SEQ ID NO 5
<211> LENGTH: 17
<212> TYPE: RNA
<213> ORGANISM: Artificial Sequence
<220> FEATURE:
<223> OTHER INFORMATION: siRNA_sense

<400> SEQUENCE: 5
aaaaugcugg gauuacg                                         17

<210> SEQ ID NO 6
<211> LENGTH: 17
<212> TYPE: RNA
<213> ORGANISM: Artificial Sequence
<220> FEATURE:
<223> OTHER INFORMATION: siRNA_anti-sense

<400> SEQUENCE: 6
cguaauccca gcauuuu                                         17

<210> SEQ ID NO 7
<211> LENGTH: 21
<212> TYPE: RNA
<213> ORGANISM: Artificial Sequence
<220> FEATURE:
<223> OTHER INFORMATION: siRNA_sense

<400> SEQUENCE: 7
aguuucuuau caaauauccu u                                    21

<210> SEQ ID NO 8
<211> LENGTH: 21
<212> TYPE: RNA
<213> ORGANISM: Artificial Sequence
<220> FEATURE:
<223> OTHER INFORMATION: siRNA_anti-sense

<400> SEQUENCE: 8
ggauauuuga uaagaaacuu u                                    21

<210> SEQ ID NO 9
<211> LENGTH: 21
<212> TYPE: RNA
<213> ORGANISM: Artificial Sequence
<220> FEATURE:
<223> OTHER INFORMATION: siRNA_sense

<400> SEQUENCE: 9
cgaaaaugcu gggauuacgu u                                    21

<210> SEQ ID NO 10
<211> LENGTH: 21
<212> TYPE: RNA
<213> ORGANISM: Artificial Sequence
<220> FEATURE:
<223> OTHER INFORMATION: siRNA_anti-sense

<400> SEQUENCE: 10
cguaauccca gcauuuucgu u                                    21

<210> SEQ ID NO 11
<211> LENGTH: 18
<212> TYPE: RNA

```
<213> ORGANISM: Artificial Sequence
<220> FEATURE:
<223> OTHER INFORMATION: siRNA_sense

<400> SEQUENCE: 11
aucaaauauc cccgcacu                                                 18

<210> SEQ ID NO 12
<211> LENGTH: 18
<212> TYPE: RNA
<213> ORGANISM: Artificial Sequence
<220> FEATURE:
<223> OTHER INFORMATION: siRNA_anti-sense

<400> SEQUENCE: 12
agugcgggga uauuugau                                                 18

<210> SEQ ID NO 13
<211> LENGTH: 18
<212> TYPE: RNA
<213> ORGANISM: Artificial Sequence
<220> FEATURE:
<223> OTHER INFORMATION: siRNA_sense

<400> SEQUENCE: 13
ccgaaaaugc ugggauua                                                 18

<210> SEQ ID NO 14
<211> LENGTH: 18
<212> TYPE: RNA
<213> ORGANISM: Artificial Sequence
<220> FEATURE:
<223> OTHER INFORMATION: siRNA_anti-sense

<400> SEQUENCE: 14
uaaucccagc auuuucgg                                                 18
```